Figure 1:
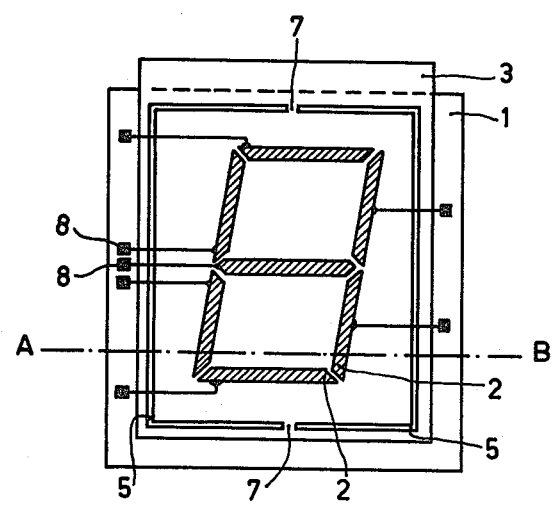

United States Patent [19]
de Zwart et al.

[11] 4,089,588
[45] May 16, 1978

[54] NEMATIC LIQUID CRYSTALLINE MIXTURE OF α-CYANOSTILBENES AND APPLICATION THEREOF IN IMAGE DISPLAY DEVICES

[75] Inventors: Maarten de Zwart; Theodorus Wilhelmus Lathouwers, both of Eindhoven, Netherlands

[73] Assignee: U.S. Philips Corporation, New York, N.Y.

[21] Appl. No.: 725,169

[22] Filed: Sep. 21, 1976

[30] Foreign Application Priority Data

Sep. 25, 1975 Netherlands .................. 7511277

[51] Int. Cl.$^2$ ..................... C09K 3/34; G02F 1/13
[52] U.S. Cl. ................................. 350/350; 252/299; 252/408
[58] Field of Search .................... 252/299, 408; 350/160 LC

[56] References Cited

U.S. PATENT DOCUMENTS 3,767,289  10/1973  Aviram et al. ............... 252/408
4,011,008  3/1977  Gerritsma et al. ............ 350/160 LC

FOREIGN PATENT DOCUMENTS 2,338,542  2/1974  Germany ..................... 252/299
2,024,269  12/1971  Germany ..................... 252/299
7,305,413  10/1974  Netherlands .................. 252/299

OTHER PUBLICATIONS

Van Der Veen; J., et al., Mol. Cryst. Liq. Cryst., Vol. 27, pp. 251–257(1974).
Hsu; E., et al., Mol. Cryst. Liq. Cryst., Vol. 27, pp. 95–104 (1974).

Primary Examiner—Benjamin R. Padgett
Assistant Examiner—T. S. Gron
Attorney, Agent, or Firm—Frank R. Trifari; Norman N. Spain

[57] ABSTRACT

Nematic liquid crystalline mixtures of α-cyanostilbenes with negative electric anisotropy which are nematic liquid crystalline in a temperature range around room temperature. The mixtures contain the compounds 2-(p-ethoxyphenyl)-3-(p-hexyloxyphenyl)-acrylonitrile and 2-(p-butoxyphenyl)-3-(p-heptylphenyl)-acrylonitrile or the compounds 2-(p-butoxyphenyl)-3-(p-pentyloxyphenyl)-acrylonitrile and 2-(p-methoxyphenyl)-3-(pentylphenyl)acrylonitrile and are very suitable for practical application in picture display devices.

5 Claims, 2 Drawing Figures

U.S. Patent  May 16, 1978  4,089,588

NEMATIC LIQUID CRYSTALLINE MIXTURE OF α-CYANOSTILBENES AND APPLICATION THEREOF IN IMAGE DISPLAY DEVICES

The invention relates to a nematic liquid crystalline mixture with negative dielectric anisotropy ($\Delta\epsilon = \epsilon_\parallel - \epsilon_\perp$) which contains at least two nematic liquid crystalline α-cyanostilbene compounds, as well as to the application of such a mixture in an image display device comprising two supporting plates with a transparent wall part and being provided with electrodes and means to supply a direct voltage or an alternating voltage to at least two of the said electrodes.

Liquid crystalline α-cyanostilbene (or 2,3-diphenylacrylonitrile) compounds are disclosed in German Offenlegungsschrift No. 2,338,542 in the name of Applicant. They are substances which correspond to the general formula

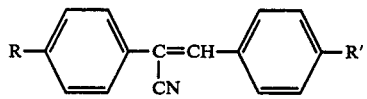

wherein R and R' are an alkyl group having 3-8 C-atoms, an alkoxy group having 1-8 C-atoms or an acyloxy group having at most 10 C-atoms. In the above-mentioned Offenlegungsschrift many compounds belonging to the above group are mentioned specifically, including the compound 2-(p-ethoxyphenyl)-3-(p-hexyl-oxyphenyl)-acrylonitrile having a melting point of 53.5°–54° C and a nematic-isotropic transition point of 80° C, as well as the substance 2-(p-butoxyphenyl)-3-(p-pentyloxyphenyl)-acrylonitrile having a melting point of 46°–47° C and a transition point of 70° C. Although the German Offenlegungsschrift also mentions the application of mixtures of compounds, the text does not comprise any further indications in this respect.

From the table stated on page 5 of the above-mentioned Offenlegungsschrift it can be derived that the melting points of the specific α-cyanostilbene compounds mentioned therein are rather high and well above room temperature. Furthermore, the transition points nematic-isotropic are in many cases rather close to the melting points; in some cases the transition point lies at a lower temperature than the melting point. All this implies that the use of the known α-cyanostilbene compounds in a display device is possible only at high temperatures, higher than room temperature, and further over a comparatively narrow temperature range. Of course, this has significantly practical objections.

Applicants have now succeeded in developing mixtures of α-cyanostilbene compounds which are nematic liquid crystalline at temperatures which are well below room temperature and the transition points nematic-isotropic of which are considerably above room temperature. For these reasons these mixtures are extremly suitable for the practical application in picture display devices.

The invention relates more in particular to a nematic liquid crystalline mixture of at least two α-cyanostilbene compounds with negative electric anisotropy and is characterized in that the mixture is nematic liquid crystalline in a temperature range around room temperature and comprises the compounds 2-(p-ethoxyphenyl)-3-(p-hexyloxyphenyl)-acrylonitrile and 2-(p-butoxyphenyl)-3-(p-heptylphenyl)-acrylonitrile or the compounds 2-(p-butoxyphenyl)-3-(p-pentyloxyphenyl)-acrylonitrile and 2-(p-methoxyphenyl)-3-(p-pentylphenyl)-acrylonitrile.

The liquid crystalline mixture according to the invention is colourless, can withstand heat and moisture and produces a dynamic scattering when arranged in an electric voltage field.

In a favourable embodiment the weight ratio between the compound 2-(p-methoxyphenyl)-3-(p-pentylphenyl)-acrylonitrile and the compound 2-(p-butoxyphenyl)-3-(p-pentyloxyphenyl)-acrylonitrile in one mixture according to the invention is of the order of magnitude of 2 : 1. The same also applies to the weight ratio between the compound 2-(p-butoxyphenyl)-3-(p-heptylphenyl)-acrylonitrile and the compound 2-(p-ethoxyphenyl)-3-(p-hexyloxyphenyl)-acrylonitrile in the other mixture according to the invention.

The composition of preferred mixtures according to the invention, as well as the associated melting points and transition points nematic-isotropic, are recorded in the following table.

TABLE

| Mixture No. | Compound of the formula R—⌬—C(CN)=CH—⌬—R' | | Weight ration between compounds in % | Melting point in °C | Transition point nematic-isotropic in °C |
|---|---|---|---|---|---|
| | R | R' | | | |
| 1 | $OCH_3$ | $C_5H_{11}$ | 68 | 8 | 42 |
|   | $OC_4H_9$ | $OC_5H_{11}$ | 32 | | |
| 2 | $OC_4H_9$ | $C_7H_{15}$ | 68 | 15 | 58 |
|   | $OC_2H_5$ | $OC_6H_{13}$ | 32 | | |

It is very well possible to incorporate in a mixture according to the invention other nematic liquid crystalline substances with negative electric anisotropy in addition to the above mentioned α-cyanostilbene compounds. Such other substances are, for example, other α-cyanostilbene compounds described in the above-mentioned Offenlegungsschrift No. 2,338,542. It should be recognized that such an addition does influence the melting point and the transition point of the mixture so that the quantity by weight of the added compound(s) should as a rule be small as compared with the quantity by weight of the α-cyanostilbene compounds already present, for example, smaller than 10% by weight.

In a further very favorable embodiment the mixture according to the invention also comprises an optically active material which when using the mixture in a display device causes a memory effect in the device. Such a memory effect means that the information recorded in a display device by means of a direct voltage or an alternating voltage is maintained after switching off the voltage.

Optically active materials known and readily useful for said purpose are cholesteric liquid crystalline compounds of which many are described in literature, for example, in U.S. Pat. Nos. 3,642,348; 3,666,947; 3,680,950; 3,705,056; 3,806,230 and 3,842,275. As examples of cholesteric liquid crystalline compounds may be mentioned: cholesteryl chloride, cholesteryl acetate, cholesteryl propionate, cholesteryl-n-butyrate, cholesteryl nonanoate, cholesteryl laurate, cholesteryl oleate, cholesteryl benzoate, cholesteryl cinnamate, cholesteryl decanoate and cholesteryl oleylcarbonate.

The quantity of an optically active substance with memory effect in the mixture according to the invention is maximum approximately 10% by weight calculated on the quantity by weight of α-cyanostilbene compounds and in most of the cases is approximately 2 to 8%.

The invention furthermore relates to an image display device which has two supporting plates having electrodes and a transparent wall part, a nematic liquid crystalline material having negative electric anisotropy between the supporting plates, as well as means to supply a direct voltage or an alternating voltage to at least two of the said electrodes.

From applicant's Dutch Patent Application No. 7,305,413, laid open to public inspection, a picture display device of the above-mentioned type is known in which a mixture of an α-cyanostilbene compound, as described in the already mentioned German Offenlegungsschrift No. 2,338,542, and an optically active substance with memory effect is used as a liquid crystalline material.

This device has the same practical drawback of a comparatively high operating temperature and a comparatively small useful temperature range as already noted with respect to the German Offenlegungsschrift No. 2,338,542.

The device according to the invention does not exhibit this drawback and is characterized in that the nematic liquid crystalline material comprises the compounds 2-(p-ethoxyphenyl)-3-(p-hexyloxyphenyl)-acrylonitrile and 2-(p-butoxyphenyl)-3-(p-heptylphenyl)acrylonitrile or the compounds 2-(p-butoxyphenyl)-3-(p-pentyloxyphenyl)-acrylonitrile and 2-(p-methoxyphenyl)-3-(p-pentylphenyl)-acrylonitrile.

Of course, in addition to the said α-cyanostilbene compounds, an optically active substance with memory effect may also be used in the device according to the invention.

The substances 2-(p-methoxyphenyl)-3-(p-pentylphenyl)-acrylonitrile and 2-(p-butoxyphenyl)-3-(p-heptylphenyl)-acrylonitrile used in the mixture and the display device according to the invention are novel compounds. The invention also relates to said novel substances and furthermore to methods for the synthesis thereof.

The new substances can be prepared according to methods which are known per se for the synthesis of similar materials or are analogous thereto.

For example, the novel substances according to the invention can be prepared by reacting a compound of formula

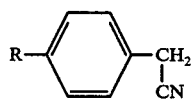

wherein R is a methoxy group or a butoxy group, with a compound of formula

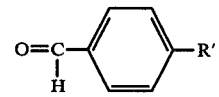

wherein R' is a pentyl group or a heptyl group. The reaction is carried out in the presence of a base, for example, KOH, NaOC$_2$H$_5$, piperidine and the like, and preferably in an inert solvent, for example alcohols such as methanol, ethanol and mixtures of alcohols and water. The reaction temperature may vary from 20° to 80° C but usually is room temperature. The above-mentioned phenyl-acetonitrile starting material can be prepared in the usual manner by converting p-hydroxyphenylacetonitrile with a strong base, such as KOH and in the presence of a solvent, for example methanol, into the corresponding potassium salt and treating the resulting product at elevated temperatures with methyliodide or butyliodide in the presence of a solvent, for example dimethyl formamide.

The above-mentioned benzaldehyde starting material can be obtained according to a method known from J. Org. Chem. 37, pp. 3972, 3973 (1972).

For this purpose, pentylbenzene or heptylbenzene is treated with trifluoroacetic acid and hexamethylene tetramine.

The invention will be described in greater detail with reference to the following specific examples.

1. Preparation of 2-(p-butoxyphenyl)-3-(p-heptylphenyl)-acrylonitrile.

(a) Synthesis of p-butoxyphenylacetonitrile.

13.3. g of p-hydroxyphenylacetonitrile and 7 g of KOH are dissolved in 200 ml of methanol. The solution is evaporated to dryness and the residue is recrystallized a few times from a mixture of benzene and ethanol. The resulting product which is the potassium salt of p-hydroxyphenylacetonitrile is added to a solution of 18.2 g of butyliodide in 250 ml of dimethyl formamide. The whole is heated at 110° C for 1 hour, after which 4 g of butyl/iodide are added and the whole is heated for the second time for 3 hours at 110° C. The reaction mixture is poured in water and extracted with petroleum ether. Yield 12.5 g of p-butoxyphenylacetonitrile.

(b) Synthesis of 4-heptylbenzaldehyde 88 g of n-heptylbenzene are taken up in 50 ml of trifluoroacetic acid and 70 g of hexamethylenetetramine. The whole is refluxed for 12 hours after which the excess of trifluoroacetic acid is distilled off by means of a water jet airpump. The mixture is then poured in ice water and neutralized with soda. After extraction with ether the resulting ether solution is evaporated and the resulting 4-heptylbenzaldehyde is used for the following process step.

(c) 2-(p-butoxyphenyl)-3-(p-heptylphenyl)-acrylonitrile.

9.4 g of p-butoxyphenylacetonitrile and 10.2 g of p-heptylbenzaldehyde are dissolved in 30 ml of methanol. 5 ml of a 40% solution of benzyltrimethylammoniumhydrate in water are added to the solution. The whole is heated at 70° C for 30 minutes and then cooled. The precipitate is sucked off and recrystallized from successively methanol and petroleum ether (60 : 80).

Melting point of the resulting compound is 34.5°–35.5.° C.

In a corresponding manner the compound 2-(p-methoxyphenyl)-3-(p-pentylphenyl)-acetonitrile was prepared. Melting point of this substance is 37–37.5° C.

2. Application of a Mixture According to the Invention in a Picture Display Device.

Figure 2:
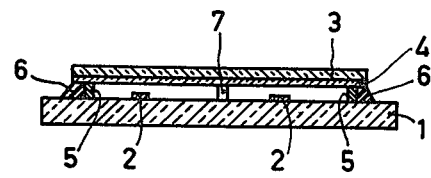

FIG. 1 is a plan view of a picture display device, and
FIG. 2 is a cross-sectional view taken on the line A—B in FIG. 1.

Reference numeral 1 in FIGS. 1 and 2 denotes a glass plate, dimensions 60 × 65 × 2 mm. An 8-shaped indium oxide pattern constructed from seven segments 2 is provided on the glass plate 1 in a thickness of 0.1 μm. A second glass plate 3, dimensions 50 × 60 × 1 mm, which is covered with a tin oxide layer 4 (FIG. 2), in a thickness of 0.1 μm, is provided after the interposition of two strips of polyethylene in a thickness of 20 μm, over glass plate 1 and connected thereto by an epoxy adhesive 6. The strips 5 do not adjoin but leave filling apertures 7 free. Via an aperture 7 the space between the glass panes is filled with a mixture which consists of 64% by weight of 2-(p-methoxyphenyl)-3-(p-pentylphenyl)-acrylonitrile or 2-(p-butoxyphenyl)-3-(heptylphenyl)-acrylonitrile and 30% by weight of 2-(p-butoxyphenyl)-3-(p-pentoxyphenyl)-acrylonitrile or 2-(p-ethoxyphenyl)-acrylonitrile and furthermore 6% by weight of cholesteryl nonanoate. The apertures are then closed with adhesive.

Current supply wires are provided on the indium oxide connection points 8 as well as on the part of glass plate 3 projecting beyond the glass plate 1.

An alternating voltage of 25 V 50 Hz is applied across the glass plate 3 and the segments of glass plate 1. An 8-shaped picture is formed which is constructed from seven lines scattering the incident light against a transparent background. After removing the voltage the picture is maintained. The picture was erased in a simple manner and vary rapidly by applying a high frequency alternating voltage field of 2000 Hz, 35 V.

What is claimed is:

1. A liquid crystalline material comprising a nematic liquid crystalline mixture of α-cyanostilbene compounds with negative electric anisotropy, characterized in that in a temperature range around room temperature the mixture is nematic liquid crystalline and contains the compounds 2-(p-ethoxyphenyl)-3-(p-hexyloxyphenyl)-acrylonitrile and 2-(p-butoxyphenyl)-3-(p-heptylphenyl)-acrylonitrile in a weight ratio of about 1 to 2 or the compounds 2-(p-butoxyphenyl)-3-(p-pentyloxyphenyl) acrylonitrile and 2-(p-methoxyphenyl)-3-(p-pentylphenyl) acrylonitrile in a weight ratio of about 1 to 2.

2. A mixture as claimed in claim 1, characterized in that the mixture contains 68% by weight of 2-(p-methoxyphenyl)-3-(p-pentylphenyl)-acrylonitrile and 32% by weight of 2-(p-butoxyphenyl)-3-(p-pentyloxyphenyl)-acrylonitrile.

3. A mixture as claimed in claim 1, characterized in that the mixture contains 68% by weight of 2-(p-butoxyphenyl)-3-(p-heptylphenyl)-acrylonitrile and 32% by weight of 2-(p-ethoxyphenyl)-3-(p-hexyloxyphenyl)-acetonitrile.

4. A memory effect liquid crystalline material comprising the material of claim 1 and up to 10% by weight of a cholesteric liquid crystalline compound.

5. An image display device comprising two electrodes at least one of which is transparent, a nematic liquid crystalline material as defined by claim 1 disposed between said electrodes and means for providing an electric field between said electrodes thereby causing said nematic liquid crystalline material subjected to said field to undergo rearrangement of the nematic liquid crystals thereby resulting in dynamic light scattering.

* * * * *